United States Patent
Mihaljevic et al.

(10) Patent No.: US 6,734,300 B2
(45) Date of Patent: May 11, 2004

(54) ACARBOSE PURIFICATION PROCESS

(75) Inventors: Kreso Mihaljevic, Zagrob (HR); Jasna Azaric, Zagreb (HR); Blazenko Bajic, Zagreb (HR); Vladimir Mrsa, Zagreb (HR); Dejana Kokanj, Zagreb (HR)

(73) Assignee: VA, Farmaceutska Industrija, DD, Zagreb (HR)

( * ) Notice: Subject to any disclaimer, the term of this patent is extended or adjusted under 35 U.S.C. 154(b) by 0 days.

(21) Appl. No.: 10/279,560

(22) Filed: Oct. 24, 2002

(65) Prior Publication Data

US 2003/0109688 A1 Jun. 12, 2003

(51) Int. Cl.$^7$ ................................................. C07H 1/06
(52) U.S. Cl. ..................... 536/127; 536/18.7; 536/17.2; 536/55.3
(58) Field of Search ............................... 536/127, 18.7, 536/17.2, 55.3

(56) References Cited

U.S. PATENT DOCUMENTS

| | | |
|---|---|---|
| 3,876,766 A | 4/1975 | Frommer et al. |
| 3,879,546 A | 4/1975 | Frommer et al. |
| 4,019,960 A | 4/1977 | Frommer et al. |
| 4,062,950 A | 12/1977 | Frommer et al. |
| 4,174,439 A | 11/1979 | Rauenbusch et al. |
| 4,526,784 A | 7/1985 | Heiker et al. |
| 4,536,493 A | 8/1985 | Junge et al. |
| 4,666,776 A | 5/1987 | Lange et al. |
| 4,767,850 A | 8/1988 | Lange et al. |
| 4,904,769 A | 2/1990 | Rauenbusch |
| 2002/0111320 A1 | 8/2002 | Keri et al. |
| 2002/0183262 A1 | 12/2002 | Keri et al. |

FOREIGN PATENT DOCUMENTS

| | | | |
|---|---|---|---|
| DE | 2347782 | | 10/1975 |
| WO | WO 99/07720 | * | 2/1999 |
| WO | 01/30796 | WO | 5/2001 |
| WO | 02/12256 | WO | 2/2002 |

OTHER PUBLICATIONS

M. P. Deutscher, "Guide to Protein Purification", Methods in Enzymology, vol. 182 (1990), Chapter 24, E. F. Rossomando, "Ion–Exchange Chromatography", Principles of Operation, p. 310.
F. de Dardel and T.V. Arden, Ion Exchange, Principles and Applications (1989), Rohm and Haas Separation Technologies, Chapter 8.1, "Description of the Ion–Exchange Cycle", p. 422–423.
Friedrich Helfferich, "Ion Exchange" (1962), Chapter 5.3, "Sorption of Solutes", p. 125, unabridged and unaltered republication, 1995.
Amersham Biosciences: "Sepharose ® Media", Data File 3100, pp. 2–5.

* cited by examiner

Primary Examiner—Samuel Barts
Assistant Examiner—Michael C. Henry
(74) Attorney, Agent, or Firm—Darby & Darby

(57) ABSTRACT

An improved process for the purification of crude aqueous solutions of acarbose by passing such solutions through a strong acid cation-exchange resin, saturating such resin and recovering as an eluate a substantially pure acarbose solution. Purities of more than 98%, and preferably about 99% or higher, are thus obtained.

19 Claims, No Drawings

ACARBOSE PURIFICATION PROCESS

BACKGROUND OF THE INVENTION

Acarbose is a polyglucose-based tetramer oligosaccharide obtained by fermentation of the microorganism Actinoplanes sp. (particularly A. utahensis). Its full chemical name is O-4,6-dideoxy-4-[[(1S,4R,5S,6S)-4,5,6-trihydroxy-3-(hydroxymethyl)-2-cyclohexen-1-yl]amino]-α-D-glucopyranosyl-(1→4)-O-α-D-glucopyranosyl-(1→4)-D-glucose. Acarbose is a white powder having a molecular weight of 645.6. It is freely soluble in water, and its pKa value is 5.1.

Acarbose's empirical formula is $C_{25}H_{43}NO_{18}$; its structural formula is:

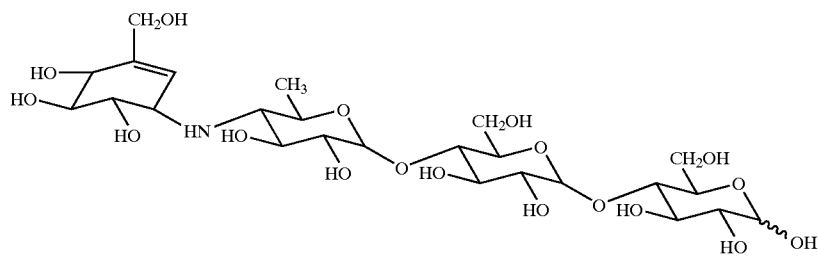

As can be seen from the structural formula, acarbose is a complex oligosaccharide consisting of two glucoses, one deoxyglucose and one dideoxy glucose derivative. The first three monomeric units are bound by O-glycosidic links, while the fourth monomeric unit is bound by an N-glycosidic linkage.

Due to the above structure, the acarbose molecule acts as an antihyperglycemic, which is a consequence of competitive reversible inhibition of the pancreatic α-amylase enzyme and the alimentary tract's α-glucosidohydrolase ($Ki \cong 10^{-12}$ M). This inhibition decreases and postpones the breakdown of ingested carbohydrates, thus decreasing the elevation of blood sugar levels after meals. In type II diabetes, the enzymatic inhibition results in postponed glucose absorption and prevention of hyperglycemia after meals. Acarbose is available on the European market as Glucobay™, and in the United States as Precose™.

Acarbose is obtained by fermentation of a microorganism of the family Acitonoplanaceae, preferably a strain of the genus Actinoplanace, followed by isolation from the fermentation broths by filtration and precipitation. See, for example, U.S. Pat. Nos. 3,876,766; 3,879,546; 4,019,960; and 4,062,950. The purity of the crude acarbose thus produced is inadequate for pharmaceutical use and, therefore, additional purification is necessary to provide the high degree of purity required for clinical application.

As noted above, the fourth glycosidic unit in the acarbose molecule is bound by the N-glycosidic link, imparting weakly basic properties to the molecule. Purification procedures for acarbose previously described in the literature were based on the use of cation-exchangers for adsorbing the acarbose molecule to the binding groups thereon; such groups do not adequately bind the weakly basic acarbose, which accordingly, results in impure acarbose products in the effluent streams therefrom. For example, purification processes have been described (see DE 2,347,782 and U.S. Pat. No. 4,174,439) in which, after the initial treatment of the culture broth with activated carbon, acarbose is bound to strong acid cation-exchangers and eluted with salt solutions or dilute acids. These exchangers are gels of the macroreticular type based on cross-linked polystyrene, which have poor mass transfer and exhibit broad peaks upon elution, resulting in relatively low product purities. Acarbose products obtained from these processes, after neutralization with basic anion exchangers, are said to have acarbose contents of about 78–88% in the dry matter (by HPLC analysis).

U.S. Pat. Nos. 4,767,850 and 4,666,776 disclose the purification of acarbose solutions by adsorption to strong acid macroporous cation echange resins based on aromatic compounds possessing one or more vinyl groups and at least one hydrophilic monomer.

U.S. Pat. No. 4,904,769, on the other hand, describes an acarbose purification method, using a chromatographic column packed with a weakly acid cation-exchanger having carboxyl binding groups thereon and based on dextran, agarose or cellulose or exchangers which are derived from such exchangers by the addition of polyacrylamide. This patent states that use of the particular purification technique thereof results in acarbose contents of at least 90% and up to as much as 98% by HPLC analysis of the dry matter. It further discloses that the acarbose products thereof contain less than 10%, and preferably 2 to 5% by weight of sugar-like secondary components. During prosecution of the patent it was asserted that strongly acidic cation exchangers could not be utilized to obtain acarbose of such purities.

The method described in U.S. Pat. No. 4,904,769 is, however, difficult to use on a production scale because acarbose is not bound but rather slowed in passing through the column. Moreover, the efficacy of such method depends on a number of factors, including the temperature of the exchanger and the pH range of the acarbose feed, which must be adjusted to optimize purification. In addition, this method involves relatively high cost due to the necessity to use highly pre-purified acarbose crudes and expensive weak acid cation-exchangers.

In International Published Application WO 99/07720 a further acarbose purification method is described, based on the use of non-aromatic strong acid cation-exchanger column chromatography. Exchangers that are hydrophilic and have high mass transfer are disclosed, e.g., a polymer-coated alumina matrix, a sulfoxyethyl cellulose resin or a methacrylate copolymer sulfonate resin. The elution of acarbose products from the column is carried out with ammonia, sodium hydroxide or hydrochloric acid. In the only example of this application, an acarbose product said to possess 98% purity is described. However, it is known that the pH values of such eluates trigger partial acarbose degradation caused by hydrolysis of glycosidic links, and are, therefore, undesirable.

In International Published Application WO 01/30796 an acarbose purification technique is disclosed, utilizing a monodispersed cross-linked polystyrene-based gel strong acid cation exchanger having a hexagonal bed structure and containing a sulfate group. The eluate from such exchanger is obtained with diluted hydrochloric acid (pH 1.0–3.0) to remove remaining salts, sugar-like secondary components and acarbose analogs. The acarbose thus obtained is said to have high purity, not less than 98%.

Yet a further acarbose purification method is disclosed in International Patent Application WO 02/12256. This application describes purifying acarbose employing a strong acid cation-exchanger, e.g., an exchanger incorporating sulfo, sulfomethyl or sulfopropyl groups, in the presence of an anion of a weak acid. The application states that the impurities present in the acarbose fermentation broth cannot adsorb onto the strong acid cation-exchanger when the anion of a weak acid is present in solution. Consequently, only acarbose is said to selectively adsorb onto the strong acid cation-exchanger, resulting in an acarbose product of assertedly high purity containing less than 1% of acarbose-related substances after drying. However, the process described in this application is relatively complex, involving the use of multiple chromatographic columns, using strong cation exchangers in the presence of an anion of a weak acid, and elution with solutions having differing specific pH ranges.

As will be apparent from the preceding background discussion, various of the previously described acarbose purification methods utilize multi-step, complex processes involving the use of both cation exchangers and anion exchangers, and either basic or acidic eluates. The use of such eluates introduces additional ions into the purified acarbose solution and requires subsequent adjustment of pH. The use of multi-step processes additionally imposes substantial additional cost, and may require highly pre-purified acarbose crude feed reactant streams.

Accordingly, it is a primary object of the present invention to provide a relatively simple, direct and economical process for the purification of acarbose, by which that product is produced in purities.

SUMMARY OF THE INVENTION

The present invention relates to a process for the purification of aqueous solutions of crude acarbose, of at least 80% by weight acarbose, which comprises:

(a) passing an aqueous solution of the crude acarbose having a pH value from about 5 to about 7 through a chromatographic column filled with a strong acid cation exchange resin, resulting in binding of acarbose and related impurities from the solution to the active exchanger groups on the resin;

(b) determining that the strong acid cation-exchange resin is saturated when the eluate from the column contains acarbose of at least 98% purity;

(c) flowing additional aqueous solution of crude acarbose through the saturated strong acid cation-exchange resin, impurities in the said solution replacing acarbose at the active exchanger groups of the resin;

(d) collecting at least the fractions of the eluate removed from the column in step (c) containing at least 98% pure acarbose; and (e) recovering and drying the purified acarbose product containing at least 98% pure acarbose from step (d).

Utilizing the process of the invention it is possible to produce substantially pure acarbose that has an acarbose content of more than 98% and, preferably, more than 99% acarbose.

The superior acarbose purities obtained by the purification process of the present invention are attributable to saturation of the strong acid cation-exchange resin with the acarbose and related sugar-like impurities from the aqueous solution of crude acarbose, followed by the formation of an eluate containing higher acarbose purities than achieved in prior art processes. It is believed that the sugar-like impurities contained in the crude acarbose solutions bind more strongly to the active exchanger groups on the strong acid cation-exchange resin than the acarbose molecules. Continued flow of the crude acarbose-containing solution then effects replacement of the acarbose molecules bound to the saturated resin with the sugar-like impurities and concomitant increased purity of the acarbose released from the resin and removed from the column in the eluate. The foregoing reaction mechanism is believed to be responsible for the superior acarbose purities obtained in the purification process hereof; however, it will be understood that the invention is not limited to the adsorption mechanism thus postulated.

By determining purities of the collected successive fractions obtained by flowing additional aqueous solution of crude acarbose through the saturated strong acid cation-exchange resin, it is possible to select the fractions containing substantially pure acarbose. Moreover, in accordance with a preferred way of carrying out the process of this invention, when the purity of the eluate decreases below desired levels, the saturated strong acid cation-exchanger is washed with pure water and those fractions of the water wash removed from the chromatographic column containing at least 98%, and preferably more than 99%, acarbose are collected and admixed with the eluate fractions obtained by flowing additional aqueous solution of crude acarbose through the saturated stron gacid cation-exchange resin. In this manner, increased product yields of the desired substantially pure acarbose product are obtained.

In accordance with additional preferred techniques for carrying out this purification process, the saturated column may additionally be eluted with dilute aqueous salt solutions containing from about 0.03 M to about 0.6M NaCl or about 0.02M to about 0.2M $NH_4OH$, and recovering those eluate fractions containing substantially pure acarbose which are removed from the column after passing either or both of these additional eluting agents therethrough. In this manner, the quantity of the substantially pure acarbose produced in accordance with the process of the invention may be further augmented.

The preceding and other preferred embodiments and advantages of this invention will be apparent from the following detailed description of the invention and various preferred embodiments thereof.

DETAILED DESCRIPTION

In this specification and the claims appended hereto, the following terms are used as noted below:

"Aqueous solutions of crude acarbose" are intended to refer to acarbose-containing solutions prepared by dissolving crude acarbose in water. Crude acarbose is obtained from the materials produced by culturing microorganism of the family Actinoplanaceae or by chemical or enzymatic hydrolysis of such material, followed optionally by preliminary purification processes in a way, for example, as described in U.S. Pat. Nos. 3,876,766; 3,879,546; 4,019,960; 4,062,950; and 4,174,439 referenced above. Crude acarbose of particular use in the purification process of the present invention may contain acarbose in excess of about 80%, and give aqueous solutions that have neutral pH values, e.g., within the range of from about 5 to about 7, preferably about 6;

"Acarbose contents or purity" is specified by weight of the pertinent acarbose material and related sugar-like substances on dry matter. The percentages specified herein have been determined by HPLC analysis as generally described in U.S. Pat. No. 4,904,769 (column 3, line 13 to column 4, line 4). The specific analyses were determined on an $NH_2$ chromatographic column, Hibar Pre-Packed Column RT250-4, LiChrosorb NH2 (5MM). In the examples set forth below the specific parameters of the analytic technique (i.e., the mobile phase, flow, temperature and detector) were based on the characteristics of that system;

"Strong acid cation-exchange resins or exchangers" refers to that class of materials described, for example, in Kirk-Othmer Encyclopedia Of Chemical Technology, Volume 14, under "Ion Exchange", pp. 737–783 (1995). Such materials remain substantially fully ionized over a wide range of pH values, as distinguished from weak acid cation-exchangers which are ionized over a small range of pH values. Strong acid cation-exchange resins useful in the present acarbose purification process have polysaccharide matrices and sulfo or sulfoalkyl (e.g., sulfomethyl, sulfoethyl or sulfopropyl) binding groups thereon. Preferred strong acid cation-exchangers useful herein include S-Sepharose Fast Flow ("FF"), SP-Sepharose Fast Flow ("FF") and Express Ion Exchanger S.

"A saturated strong acid cation-exchange resin or exchanger" refers to such a resin in which the binding groups thereon are substantially completely bound to acarbose molecules or to sugar-like impurities incorporated in crude acarbose aqueous solutions. As used herein, a strong acid cation-exchange resin employed in the purification process hereof is regarded as saturated when an eluate recovered from such resin contains substantially pure acarbose; and "Substantially pure acarbose" refers to an acarbose composition having an acarbose content or purity of more than about 98% and preferably, more than about 99%, of the weight of that composition after drying.

Elution of acarbose aqueous solutions from strong acid cation exchangers, in accordance with prior art procedures, generally produces varying fractions of acarbose and other sugars such as the principal related substance, the acarbose-like oligomer having one glucose unit less than acarbose. During the fermentation and isolation process of crude acarbose substantial co-production of other sugar-like impurities occurs, and because these sugar-like impurities are difficult to separate from acarbose, the preparation of substantially pure acarbose compositions by previous techniques could not be carried out in an efficient manner.

On the other hand, utilizing the purification process of the present invention, it is possible to obtain fractions in which other sugar-like impurities, eluted from a saturated, strong acid cation-exchange resin in accordance with the present invention, are typically present in negligible quantities.

Employing the purification process hereof, it is important that the aqueous solution of the crude acarbose passed into the strong acid cation-exchange resin be introduced to the chromatographic column at pH from about 5 to about 7. Employing solutions of crude acarbose of pH out of the mentioned range results in degradation of acarbose and increases the concentration of other ions, which then have to be removed in subsequent steps.

As indicated above, the purification process involves passing the crude acarbose aqueous solution through the column until the strong acid cation-exchange resin is saturated, as indicated when the eluate contains substantially pure, i.e., at least about 98%, acarbose. The purity of each successive eluate fraction removed from the column is determined by HPLC analysis of each such fraction. As additional aqueous solution of crude acarbose is flowed through the saturated cation-exchange resin, impurities in the solution replace acarbose molecules on the active exchanger groups on the resin, resulting in increased purity of the eluate. Those fractions containing substantially pure acarbose, i.e., at least about 98% and, preferably, about 99% or higher, are recovered and dried in accordance with the present process.

As further indicated hereinabove, additional substantially pure acarbose-containing solutions may be produced after flowing the crude acarbose aqueous solution through the resin, by water washing of the resin and, if desired, by eluting with an aqueous solution of NaCl having a concentration of from about 0.03 to about 0.6 M or an aqueous solution of $NH_4OH$ having a concentration of from about 0.02 to about 0.2 M, through the column. There are thus formed additional fractions of aqueous solutions containing substantially pure acarbose.

These and further modifications of the acarbose purification process of the present invention are described in the following examples.

EXAMPLES

The following examples illustrate preferred embodiments of the present invention. The examples are not intended as limiting, but solely to exemplify preferred ways for carrying out the acarbose purification process hereof. It will be understood that various changes may be made in the specific procedures described in the examples without departing from the scope of the invention.

In the experiments described in Examples 1 to 4, an aqueous soluton of crude acarbose that was passed through the adsorption column contained about 82% by weight of acarbose and had a pH of about 6 measured prior to the introduction to the column. In all of the examples the chromatographic column utilized had a diameter of 1.6 cm and a length of 12 cm connected to a peristaltic pump and an automatic fraction collector RediFrac. The chromatographic column, the peristaltic pump and the RediFrac are available from Amersham Pharmacia Biotech. After the chromatographic separations described below, the strong acid cation exchange resins in the column were regenerated by sequential washing with 0.2 M ammonium hydroxide (250 ml), distilled and degassed water (75 ml), 0.01 M HCl (500 ml) and distilled and degassed water (cca 100 ml) until the pH of the effluent reached about 7.0.

Example 1

Purification of Acarbose through an SP Sepharose FF Strong Acid Cation Exchange Resin, Water Wash and Elution With Aqueous NH4OH In this experiment, the chromatographic column was packed with SP Sepharose FF (a strong acid cation exchange resin having a polysaccharide cross-linked agarose matrix and sulfopropyl active groups, available from Amersham Pharmacia Biotech) to obtain a working volume $V_{resin}$ of 25 $cm^3$.

The crude acarbose (about 82% acarbose content) (2.5 g) was dissolved in distilled, degassed water to provide 125 ml of crude acarbose solution. The solution was passed through the column at a 100 ml/hr flow rate, followed by 250 ml of distilled, degassed water. The total collected volume from passing the crude acarbose solution and the distilled degassed water through the column was 375 ml. This fraction (the "NP" fraction) was analyzed by HPLC and contained acarbose of 98.89% purity.

The column was thereafter eluted with 250 ml of an aqueous solution of 0.2 M NH$_4$OH yielding 5 ml. eluate fractions "E" (each 5 ml) from E-1 to E-18. Table 1 below shows that fractions E-1 to E-9 contained either pure water or small quantities of pure acarbose, and fractions E-10 to E-12 contained acarbose of high purity (more than 99%). Fractions E-13 to E-18 contained significant concentrations of acarbose related substances.

The successive acarbose fractions recovered in this manner are identified in Table 1:

TABLE 1

Acarbose Purification through Saturated SP Sepharose FF Resin, Followed by a Water Wash and Elution With Aqueous NH$_4$OH.

| Fractions | Acarbose (HPLC % area) | Main related substance (HPLC % area) | REMARKS |
|---|---|---|---|
| NP | 98.89 | 0.12 | fraction of pure acarbose |
| E-1 to E-9 | — | — | fractions with no significant amount of acarbose |
| E-10 | 99.65 | 0.06 | fraction of pure acarbose |
| E-12 | 99.76 | 0.06 | fraction of pure acarbose |
| E-13 | 93.41 | 5.89 | |
| E-14 | 64.01 | 33.03 | |
| E-15 | 48.92 | 48.26 | |
| E-16 | 44.16 | 35.24 | low concentration |
| E-18 | — | — | very low concentration |

Example 2

Purification of Acarbose through an S-Sepharose FF Strong Acid Cation-exchange Resin, Water Wash And Elution With Aqueous NH$_4$OH A chromatography column was prepared and utilized for the purification of a crude acarbose solution, utilizing substantially the same technique as described in Example 1 above but employing the strong acid cation-exchanger S-Sepharose Fast Flow. S-Sepharose Fast Flow is an exchanger with the same matrix as SP-Sepharose Fast Flow but having sulfomethyl active groups.

Crude acarbose (about 82% acarbose content) (2.5 g) was dissolved in distilled, degassed water (125 ml). The aqueous solution of crude acarbose was passed through the column at a flow rate of 100 ml/hr, followed by 250 ml of distilled, degassed water. The total collected volume from passing the crude acarbose solution and the distilled degassed water through the column was 375 ml. This NP fraction was analyzed by HPLC and contained acarbose of 98.42% purity.

The saturated column was thereafter eluted with an aqueous solution of 0.02 M NH$_4$OH (250 ml) providing eluate fractions "E" (each 5 ml), from E-1 to E-40. As shown in Table 2 fractions E-1 to E-26 contained no acarbose or related substances, whereas fractions E-27 to E-29 contained acarbose of high purity.

Acarbose contens of the respective fractions are identified in Table 2 below.

TABLE 2

Acarbose Purification Through Saturated S Sepharose FF Resin, Followed By Water Wash And Elution With Aqueous NH$_4$OH

| Fractions | Acarbose (HPLC % area) | Main related substance (HPLC % area) | REMARKS |
|---|---|---|---|
| NP | 98.42 | 0.02 | fraction of pure acarbose |
| E-1 to E-26 | — | — | fractions with no significant amount of acarbose |
| E-27 | 99.79 | 0.06 | fraction of pure acarbose |
| E-29 | 99.40 | 0.47 | fraction of pure acarbose |
| E-30 | 86.59 | 13.24 | |
| E-31 | 56.72 | 40.18 | |
| E-32 | 63.97 | 32.82 | |
| E-33 | 56.83 | 40.82 | |
| E-35 | 32.26 | 60.68 | low concentration |
| E-40 | — | — | very low concentration |

Example 3

Purification of Acarbose through Anr SP Sepharose FF Strong Acid Cation Exchange Resin, Wash with Aqueous NaCl and Elution with Aqueous NH$_4$OH A chromatography column was prepared in the same manner as described above. SP Sepharose FF was again used as the strong acid cation-exchange resin.

Crude acarbose (about 82% acarbose contet) (10.0 g) was dissolved in distilled, degassed water (220 ml). The aqueous solution of crude acarbose was applied to the column at a flow rate of 50 ml/hr, and 20 ml fractions N-1 to N-12 were collected. Fractions N-4 through N-6 together contained about 3 g of acarbose, which had a purity of about 99%. Fractions N-7 to N-12 contained lower purity acarbose from about 95% to about 97% purity) and could be used again as crude acarbose solution.

Subsequently, the column was eluted with an aqueous salt solution containing 50 mM NaCl (70 ml) at a flow rate of 17.5 ml/hr. Two fractions S-1 and S-2 (each 35 ml) were collected. Both had low acarbose purities and could be used again as crude acarbose solution after removal of chloride anions.

The column was then eluted (washed) with an aqueous solution of 0.2 M NH$_4$OH (70 ml). Eluted fractions were collected in two fractions E-1 and E-2 (each 35 ml), and these fractions contained no acarbose or related substances (See Table 3 below).

Acarbose contents in the respective fractions are identified in Table 3 below.

TABLE 3

Acarbose Purification through Saturated SP Sepharose FF Resin, Followed by Aqueous NaCl Wash and Elution With Aqueous NH$_4$OH

| Fractions | HPLC - Acarbose quality (HPLC % area) | Main related substance (HPLC % area) | REMARKS |
|---|---|---|---|
| N-1 and N-2 | — | — | fractions with no significant amount of acarbose |
| N-3 | — | — | very low concentration |
| N-4 | 98.99 | 0.19 | fraction of pure acarbose |
| N-5 | 99.18 | 0.20 | fraction of pure acarbose |
| N-6 | 99.03 | 0.52 | fraction of pure acarbose |
| N-7 | 97.33 | 2.23 | |

TABLE 3-continued

Acarbose Purification through Saturated SP Sepharose FF Resin, Followed by Aqueous NaCl Wash and Elution With Aqueous NH$_4$OH

| Fractions | HPLC - Acarbose quality (HPLC % area) | Main related substance (HPLC % area) | REMARKS |
|---|---|---|---|
| N-8 | 95.33 | 4.02 | |
| N-9 | 95.30 | 3.79 | |
| N-10 | 95.52 | 3.97 | |
| N-11 | 95.08 | 4.08 | |
| N-12 | 95.34 | 4.02 | |
| S-1 | 94.5 | 5.09 | |
| S-2 | 76.87 | 17.92 | low concentration |
| E-1 | — | — | fraction with no significant amount of acarbose |
| E-2 | — | — | — |

Example 4

Purification of Acarbose through an SP Sepharose FF Strong Acid Cation Exchange Resin, Water Wash and Elution with Aqueous NaCl A chromatography column containing SP Sepharose FF as the strong acid cation-exchanger was prepared in the same manner as described above.

Crude acarbose (1.5 g) was dissolved in distilled, degassed water (75 ml). Aqueous solution of crude acarbose was fed through the column at a flow rate of 50 ml/hr and 75 ml fraction N was collected. Subsequently, the column was washed with distilled, degassed water (250 ml) resulting in fraction P (250 ml). Fraction P contained acarbose of about 99% purity. (See Table 4 below).

Thereafter, additional acarbose from the column was collected by elution of the column with 75 ml of 50 mM aqueous oluton of NaCl at a flow rate of 17.5 ml/hr. Salt fractions S-1 to S-13 (each 5 ml) were collected and anallyzed. Fractions S-3 to S-10 contained acarbose of above 99% purity. Chloride ions contained in these fractions can easily be removed by known techniques. Fractions S-11 to S-13 had lower acarbose purities and could be used again as crude acarbose solution after removal of chloride anions.

TABLE 4

Acarbose Purification Through Saturated SP Sepharose FF Resin, Followed by Water Wash and Elution With Aqueous NaCl

| Fractions | HPLC - Acarbose quality (% area) | Main related substance (% area) | REMARKS |
|---|---|---|---|
| N | — | — | fraction with no significant amount of acarbose |
| P | 98.68 | 0.14 | fraction of pure acarbose |
| S-1 and S-2 | — | — | fractions with no significant amount of acarbose |
| S-3 | 100.00 | 0.00 | fraction of pure acarbose |
| S-6 | 99.95 | 0.03 | fraction of pure acarbose |
| S-8 | 99.76 | 0.19 | fraction of pure acarbose |
| S-9 | 99.73 | 0.22 | fraction of pure acarbose |
| S10 | 99.57 | 0.38 | fraction of pure acarbose |
| S-11 | 98.25 | 1.74 | |
| S-12 | 79.54 | 19.73 | |
| S-13 | 52.07 | 45.78 | low concentration |

It will be understood that the foregoing description of preferred embodiments of the present invention is intended as illustrative and not in a limiting sense, and that the scope of the invention is based on the following claims.

What is claimed is:

1. A process for the purification of aqueous solutions of crude acarbose containing at least 80% by weight acarbose, and sugar-like impurities, which comprises:
   (a) passing a stream comprising an aqueous solution of crude acarbose having a pH from about 5 to about 7 through a chromatographic column containing a strong acid cation-exchange resin, acarbose and the impurities in the solution binding to the active exchanger groups on the resin;
   (b) saturating the strong acid cation-exchange resin with acarbose and the impurities in the stream, the impurities in the stream binding more strongly to the active exchanger groups on the strong acid cation-exchange resin than the acarbose molecules;
   (c) flowing the stream through the saturated strong acid cation-exchange resin, the impurities in the stream replacing acarbose on the active exchanger groups of the resin;
   (d) collecting at least the fractions of the stream removed from the column in step (c) containing at least 98% acarbose; and
   (e) recovering and drying a substantially pure acarbose product containing the at least 98% acarbose collected in step (d).

2. The process of claim 1, wherein the strong acid cation-exchange resin comprises a polysaccharide matrix having sulfo or sulfoalkyl binding groups thereon.

3. The process of claim 2, wherein the sulfoalkyl binding groups are sulfomethyl, sulfoethyl or sulfopropyl groups 4. The process of claim 2, wherein the cation-exchange resin is S-Sepharose Fast Flow, SP-Sepharose Fast Flow or Express Ion Exchanger S.

5. The process of claim 1, wherein the fractions collected in step (d) and the product recovered and dried in step (e) have acarbose content of more than 99% by weight.

6. The process of claim 1, wherein after step (c), the saturated strong acid cation-exchange resin is washed with pure water and thereafter the fractions of the water wash containing at least 98% pure acarbose are recovered and dried in step (e) together with the fractions containing the at least 98% acarbose from step (d).

7. The process of claim 6, wherein subsequent to the water wash the saturated strong acid cation-exchange resin is eluted with a second stream comprising at least one eluting agent selected from the group consisting of aqueous solutions containing from 30 to 600 mM NaCl and aqueous solutions containing from 20 to 200 mM NH$_4$OH, at least the fractions of the eluates removed from the column after passing said second stream therethrough which contain the at least 98% pure acarbose are collected and admixed with the eluate fractions collected in step (d) and the fractions of the water wash containing the at least 98% pure acarbose, and the resulting mixture is recovered and dried in step (e) to produce the substantially pure acarbose product containing the at least 98% acarbose.

8. The process of claim 1, wherein subsequent to step (c) the saturated strong acid cation-exchange resin is eluted with a second stream comprising at least one eluting agent selected from the group consisting of aqueous solutions containing from 30 to 600 mM NaCl and aqueous solutions containing from 20 to 200 mM NH$_4$OH, at least theft actions of the eluates removed from the column after passing said second stream therethrough which contain at least 98% pure acarbose are collected and admixed with the fractions collected in step (d), and the resulting mixture is recovered and dried in step (e) to produce the substantially pure acarbose product containing the at least 98% acarbose.

9. A process for the purification of aqueous solutions of acarbose containing at least 80% by weight acarbose, and sugar-like impurities, which comprises:
   (a) passing a stream comprising an aqueous solution of crude acarbose having a pH of from about 5 to about 7 through a chromatographic column containing a strong acid cation-exchange resin, the acarbose and the impurities in the solution binding to the active exchanger groups on the resin;
   (b) saturating the strong acid cation-exchange resin with acarbose and the impurities in the stream, the impurities in the stream binding more strongly to the active exchanger groups on the strong acid cation-exchange resin than the acarbose molecules;
   (c) flowing the stream through the saturated strong acid cation-exchange resin, the impurities in the stream replacing acarbose on the active exchanger groups on the resin;
   (d) collecting at least the fractions of the stream removed from the column in step (c) containing at least 99% acarbose; and
   (e) recovering and drying a substantially pure acarbose product containing the at least 99% acarbose from the fractions of the stream collected in step (d).

10. The process of claim 9, wherein the strong acid cation-exchange resin comprises a polysaccharide matrix having sulfo or sulfoalkyl binding groups thereon.

11. The process of claim 10, wherein the sulfoalkyl binding groups are sulfomethyl, sulfoethyl or sulfopropyl groups.

12. The process of claim 10, wherein the cation-exchange resin is S-Sepharose Fast Flow, SP-Sepharose Fast Flow or Express Ion Exchanger S.

13. The process of claim 9, wherein after step (c) the saturated strong acid cation-exchange resin is washed with pure water and thereafter the fractions of the water wash containing at least 99% pure acarbose are recovered and dried in step (e) together with the fractions containing the at least 99% acarbose from step (d).

14. The process of claim 13, wherein subsequent to the water wash the saturated strong acid cation-exchange resin is eluted with a second stream comprising at least one eluting agent selected from the group consisting of aqueous solutions containing from 30 to 600 mM NaCl and aqueous solutions containing from 20 to 200 mM $NH_4OH$, at least the fractions of the eluates removed from the column after passing said second stream therethrough which contain at least 99% pure acarbose are collected and admixed with the eluate fractions collected in step (d) and the fractions of the water wash containing the at least 99% pure acarbose, and the resulting mixture is recovered and dried in step (e) to produce the substantially pure acarbose product containing the at least 99% acarbose.

15. The process of claim 9, wherein subsequent to step (c) the saturated strong acid cation-exchange resin is eluted with a second stream comprising at least one eluting agent selected from the group consisting of aqueous solutions containing from 30 to 600 mM NaCl and aqueous solutions containing from 20 to 200 mM $NH_4OH$, at least acarbose fractions (1) collected in step (d) and (2) collected after passing said second stream therethrough which contain at least 99% pure acarbose, are admixed and the resulting mixture is recovered and dried in step (e) to produce the substantially pure acarbose product containing the at least 99% acarbose.

16. The process of claim 1 wherein, upon saturation of the strong acid cation-exchange resin, the active exchanger groups on the resin are substantially completely bound to the acarbose molecules or to the sugar-like impurities incorporated in the aqueous solution of crude acarbose.

17. The process of claim 1 wherein, upon saturation of the cation-exchange resin, the acarbose molecules bound to the saturated resin are replaced by the sugar-like impurities in the aqueous solution of crude acarbose, resulting in increased purity of the acarbose released from the resin and removed from the column in the stream.

18. The process of claim 9 wherein, upon saturation of the strong acid cation-exchange resin, the active exchanger groups on the resin are substantially completely bound to the acarbose molecules or to the sugar-like impurities incorporated in the aqueous solution of crude acarbose.

19. The process of claim 9 wherein, upon saturation of the cation-exchange resin, the acarbose molecules bound to the saturated resin are replaced by the sugar-like impurities in the aqueous solution of crude acarbose, resulting in increased purity of the acarbose released from the resin and removed from the column in the stream.

* * * * *

UNITED STATES PATENT AND TRADEMARK OFFICE
CERTIFICATE OF CORRECTION

PATENT NO. : 6,734,300 B2
DATED : May 11, 2004
INVENTOR(S) : Kreso Mihaljevic et al.

It is certified that error appears in the above-identified patent and that said Letters Patent is hereby corrected as shown below:

<u>Title page,</u>
Item [73], Assignee, please delete "VA, Farmaceutska Industrija, DD, Zagreb (HR)" and substitute -- PLIVA, Farmaceutska Industrija, DD, Zagreb (HR) --.

Signed and Sealed this

Twenty-sixth Day of July, 2005

JON W. DUDAS
*Director of the United States Patent and Trademark Office*

UNITED STATES PATENT AND TRADEMARK OFFICE
CERTIFICATE OF CORRECTION

PATENT NO.   : 6,734,300 B2
DATED        : May 11, 2004
INVENTOR(S)  : Kreso Mihaljevic et al.

It is certified that error appears in the above-identified patent and that said Letters Patent is hereby corrected as shown below:

<u>Title page,</u>
Insert Item:
-- [30]   Foreign Application Priority Data

CROATIA       P20010792A            10/26/2001 --.

Signed and Sealed this

Twenty-fourth Day of January, 2006

JON W. DUDAS
*Director of the United States Patent and Trademark Office*